United States Patent [19]
Baumann

[11] Patent Number: 5,800,471
[45] Date of Patent: Sep. 1, 1998

[54] METHOD FOR OPTIMIZING CARDIAC PERFORMANCE BY DETERMINING THE OPTIMAL PACING MODE-AV DELAY FROM A TRANSIENT HEART RATE SIGNAL FOR USE IN CHF, BRADY, AND TACHY/BRADY THERAPY DEVICES

[75] Inventor: Lawrence S. Baumann, Bloomington, Minn.

[73] Assignee: Cardiac Pacemakers, Inc., St. Paul, Minn.

[21] Appl. No.: 953,736

[22] Filed: Oct. 20, 1997

[51] Int. Cl.⁶ ............................................. A61N 1/365
[52] U.S. Cl. ................................................... 607/25
[58] Field of Search ............................ 607/9, 25, 17, 607/18, 19, 20

[56] References Cited

U.S. PATENT DOCUMENTS

| | | |
|---|---|---|
| 5,312,452 | 5/1994 | Salo . |
| 5,334,222 | 8/1994 | Salo et al. . |
| 5,466,245 | 11/1995 | Spinelli et al. . |
| 5,487,752 | 1/1996 | Salo et al. . |
| 5,540,727 | 7/1996 | Tockman et al. . |

OTHER PUBLICATIONS

*Usefullness of Physiologic Dual–Chamber Pacing in Drug–Resistant Idiopathic Dilated Cardiomyopathy*; "The American Journal of Cardiology"; vol. 66; Jul. 15, 1990; pp. 198–202.

*Hemodynamic Effect of Physiological Dual Chamber Pacing in a Patient with End–Stage Dilated Cardiomyopathy; A Case Report*; Hajime Katoaka, M.D.; PACE, vol. 14; Sep. 1991; pp. 1330–1335.

*Primary Examiner*—Scott M. Getzow
*Attorney, Agent, or Firm*—Haugen and Nikolai, P.A.

[57] ABSTRACT

A cardiac rhythm management device includes a dual chamber pacemaker especially designed for treating congestive heart failure. The device incorporates a programmed microcontroller which is operative to adjust the pacing mode-AV delay of the pacemaker so as to achieve optimum hemodynamic performance. Atrial cycle lengths measured during transient (immediate) time intervals following a change in the mode-AV delay are signal processed and a determination can then be made as to which particular configuration yields optimum performance.

8 Claims, 6 Drawing Sheets

METHOD FOR OPTIMIZING CARDIAC PERFORMANCE BY DETERMINING THE OPTIMAL PACING MODE-AV DELAY FROM A TRANSIENT HEART RATE SIGNAL FOR USE IN CHF, BRADY, AND TACHY/BRADY THERAPY DEVICES

BACKGROUND OF THE INVENTION

I. Field of the Invention

This invention relates generally to implantable cardiac rhythm management devices, and more particularly to a method for establishing an optimum pacing mode and AV delay parameter for a dual chamber implantable, programmable pacemaker.

II. Discussion of the Prior Art

Congestive heart failure (CHF) is an insidious disease affecting at least two million Americans. Patients diagnosed with heart failure have such a poor long-term prognosis (the average life span is five years) that it is tantamount to a death sentence. Thus, the potential market for successful therapy is not only large but highly motivated.

In the past, implantable cardiac pacemakers have principally been used to treat heart rate disorders, including bradycardia and tachycardia. Marguerite Hochleitner and her co-workers in the Department of Medicine of the University of Innsbruck published a paper called "Usefulness of Physiologic Dual-Chamber Pacing in Drug-Resistant Idiopathic Dilated Cardiomyopathy" in the *American Journal of Cardiology* (Vol. 66, Jul. 15, 1990, pp. 198–202) describing a study on a series of patients as to the beneficial effects of physiologic, dual-chamber (DDD) pacing in the treatment of end-stage idiopathic dilated cardiomyopathy. The pacemakers were implanted with the atrial electrode positioned near the right auricle and the ventricular electrode in the apical region of the right ventricle. Externally microprogrammable pacemakers, allowing reprogramming of the atrioventricular (AV) interval, were used. The AV interval was set at 100 milliseconds, this value being chosen as the shortest possible AV delay which would not significantly impair cardiac function. A marked improvement in cardiac function in most of the patients in the study resulted. For example, a remarkable improvement was noted in left ventricular ejection fraction, a reduction in heart size, a decrease in heart rate with tachycardia patients and an increase in heart rate for patients with bradycardia.

The devices described in the Hochleitner paper are not capable of adjusting the AV interval to fit the patient's changing condition after implant. While they do allow a change in AV interval through external reprogramming by the physician, optimization of AV interval through closed loop control is not involved.

Current dual chamber pacemakers that allow for self-adjustment of the AV interval use an algorithm based entirely on rate. This shortening of AV interval with increased rate is merely designed to mimic the shortening of the PR interval which occurs in normal individuals with increases in rate. Patients in heart failure, however, will require adjustments in AV interval which are independent of rate and are, instead, a function of the patient's condition, posture, etc. Moreover, the AV shortening required with rate increases in these patients may not be identical to that for normal individuals.

In a paper entitled "Hemodynamic Effect of Physiological Dual Chamber Pacing in a Patient with End-Stage Dilated Cardiopathy: A Case Report" by Kataoka (*Pace*, Vol. 14, September 1991, pp. 1330–1335) describes the treatment of a patient in CHF using a DDD pacemaker. Again, the pacemaker described in this paper, while adjustable via an external transcutaneous programmer, did not provide for self-adjustment to meet changing conditions of the patient. Kataoka recommended that invasive hemodynamic measurements and a Doppler flow study be carried out to define an optimal AV interval but, as mentioned, the system described therein is basically open-loop with no feedback being provided for automatically adjusting AV interval to a value that optimizes systolic and diastolic function.

The Salo U.S. Pat. No. 5,312,452 and the Salo et al. U.S. Pat. Nos. 5,334,222 and 5,487,752 each describe particular algorithms that can be executed by a microprocessor-based implantable cardiac rhythm management device to optimize the AV delay interval when treating CHF patients. Another patent describing a system and method for optimizing AV delay is that to Spinelli et al. U.S. Pat. No. 5,466,245. That patent describes the interaction of the sympathetic and para-sympathetic tones of the autonomic nervous system in reacting to changes in the hemodynamic performance of the heart as a mechanical pump when the AV delay between cardiac stimulating pulses is changed. In particular, heart rate variability occasioned by changes in the paced AV delay interval is measured over a sufficiently long time interval that transient (short-term) variations are ignored and only steady state changes in heart rate variability are assessed.

The Tockman et al. U.S. Pat. No. 5,540,727 describes an apparatus and algorithm for optimizing both the pacing mode and the AV delay parameter for an implantable cardiac stimulating device. In implementing the algorithm, the system incorporates a physiologic sensor configured to provide an average value of that parameter over a predetermined time interval for each change in pacing mode/AV delay interval. The particular AV delay interval associated with a optimum average value of the physiologic parameter is used to establish the AV delay interval for the programmable stimulator until such time as the algorithm is again executed and a new optimum AV delay interval is established.

Based upon the prior art of which we are aware, no one has attempted to optimize cardiac performance by automatically determining the optimal pacing mode-AV delay by measuring transient (immediate) changes in ACL or VCL following a transition from an established baseline to a paced mode-AV delay. By measuring the ACL or VCL in the transient period, the optimum pacing mode-AV delay protocol can quickly cycle through a range of mode-AV delays which thereby reduces the duration of the optimization protocol.

SUMMARY OF THE INVENTION

The method of the present invention is carried out by means of a dual chamber pacemaker of the type having means for sensing atrial and ventricular depolarization events, including a microprocessor-based controller for selectively stimulating the right, the left or both ventricular chamber with pacing pulses at predetermined AV delay intervals following detection of atrial depolarization events. The microprocessor-based controller also includes means for determining atrial cycle lengths (ACL) along with a memory for storing data in an addressable array. While the invention will be described with ACL being the measured dependent variable, it should be recognized that ventricular cycle length (VCL) can also be the measured variable.

The algorithm executed by the microprocessor-based controller includes the steps of storing in the memory a listing of pacing mode and AV delay configurations where each such configuration specifies the ventricular chamber(s) to be stimulated and an AV delay interval to be utilized. The ventricular chamber(s) are then paced in accordance with a pacing mode-AV delay configuration selected randomly from the listing for a first number of beats, $N_1$, following a second number of intrinsic or paced beats, $N_2$, that are sufficient to establish a baseline. This pacing step is repeated for each pacing mode and AV delay configuration contained in the listing. For each of the $N_1$ and $N_2$ beats, the ACL (or VCL) between each such beat is computed and stored in the addressable array of the memory of the microprocessor-based controller.

The raw ACL data stored in the array is smoothed using known signal processing techniques and once this is done, a smoothed atrial cycle length feature (sACLf) is computed from each repeated instance of each pacing mode and AV delay configuration and from the immediately preceding baseline beats of the instance. These sACLfs are then processed and compared to identify the mode-AV delay configuration yielding a maximum average of the values of the atrial cycle length feature with the dual chamber pacemaker then being programmed to operate in the mode and AV delay value so determined.

In summary, then, the microprocessor-based controller of the programmable dual chamber pacemaker measures ACLs. The device cycles through beats with different pacing mode and AV delay configurations. Each configuration is defined to be a group of consecutive beats with the same paced AV delay and the same pacing mode (right ventricle paced, left ventricle paced or both ventricles paced). Each such configuration is immediately preceded by a group of baseline beats.

For each configuration, the algorithm calculates the value of the ACL for the beats of the paced mode-AV delay. The algorithm calculates the value of the atrial cycle length for the immediately preceding baseline beats. The algorithm subtracts these two values to determine the value of the change of the atrial cycle length going from baseline to the paced mode-AV delay configuration. This change value is the value of the atrial cycle length feature.

The device cycles through the different configurations a predetermined number of times and for each unique paced mode-AV delay configuration, the average of the values of the atrial cycle length feature is calculated from the several instances of that configuration in the protocol.

Next, the maximum of these averages of the values of the atrial cycle length feature is found to correspond with a particular mode-AV delay configuration. Based upon research which we have conducted, this mode-AV delay configuration which gives the maximum average of the values of the atrial cycle length feature is also the optimal mode-AV delay configuration which is defined to be the mode-AV delay configuration which gives the maximum average of the change values of the hemodynamic parameter feature, e.g., aortic pulse pressure. Thus, the optimal mode-AV delay configuration is identified.

DESCRIPTION OF THE DRAWINGS

The foregoing features, objects and advantages of the present invention will become apparent to those skilled in the art from the following detailed description of a preferred embodiment, especially when considered in conjunction with the accompanying drawings in which.

DESCRIPTION OF THE PREFERRED EMBODIMENT

Figure 1:
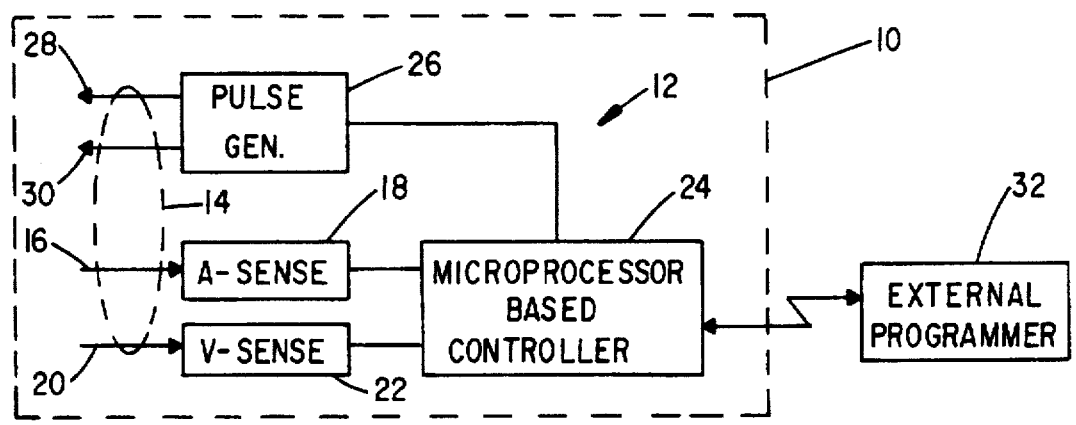
FIG. 1 is a schematic block diagram of a dual chamber pacemaker incorporating a microprocessor-based controller in which the AV delay parameter is optimized in accordance with the algorithm disclosed herein.

Referring first to FIG. 1, there is shown enclosed by a dashed-line box 10, a cardiac rhythm management device, here depicted as a VDD bradycardia pacemaker 12, which is adapted to be operatively coupled to a patient's heart by means of a conventional pacing lead 14. In particular, an atrial sensing electrode disposed in the right atrium of the heart is coupled by a wire 16 in the lead 14 to an atrial sense amplifier 18. Similarly, a ventricular sensing electrode disposed in the right ventricle is connected by a wire 20 in the lead 14 to a ventricular sense amplifier 22 contained within the pacemaker 12. Thus, when the SA node in the right atrium depolarizes, the resulting signal is picked up by the atrial sense amplifier 18 and applied to a microprocessor-based controller 24 which will be more particularly described with the aid of FIG. 2. Ventricular depolarization signals (R-waves) are likewise amplified by the ventricular sense amplifier 22 and applied as an input to the microprocessor-based controller 24.

The microprocessor-based controller 24 is connected in controlling relationship to a pulse generator 26 to cause a ventricular stimulating pulse to be applied, via conductor 28 in lead 14, to tissue located proximate the apex of the right ventricle (RV) to initiate ventricular depolarization that spreads as a wave across both the right and left ventricles. The pulse generator 26, under control of the microprocessor-based controller 24, can also be made to apply stimulating pulses over a wire 30 in lead 14 to stimulate the heart's left ventricle (LV). If the pacing mode calls for biventricular pacing, the pulse generator 26 is controlled by the microprocessor-based controller 24 to deliver stimulating pulses to both the right and left ventricles (BV).

The microprocessor-based controller 30 not only controls the rate at which cardiac stimulating pulses are produced, but also the timing thereof relative to a preceding atrial depolarization signal to thereby define an AV interval.

An external programmer 32 is arranged to send data signals transcutaneously to the implanted pacemaker 12 and also to receive signals originating within the pacemaker. In this fashion, a physician is capable of programming such parameters as pacing rate, pacing pulse width, pacing pulse amplitude, sensitivity, AV delay interval, etc., in a fashion known in the art. The external programmer may also be used to receive signals and pass them on to an external monitor (not shown) incorporating a microprocessor and associated memory.

Figure 2:
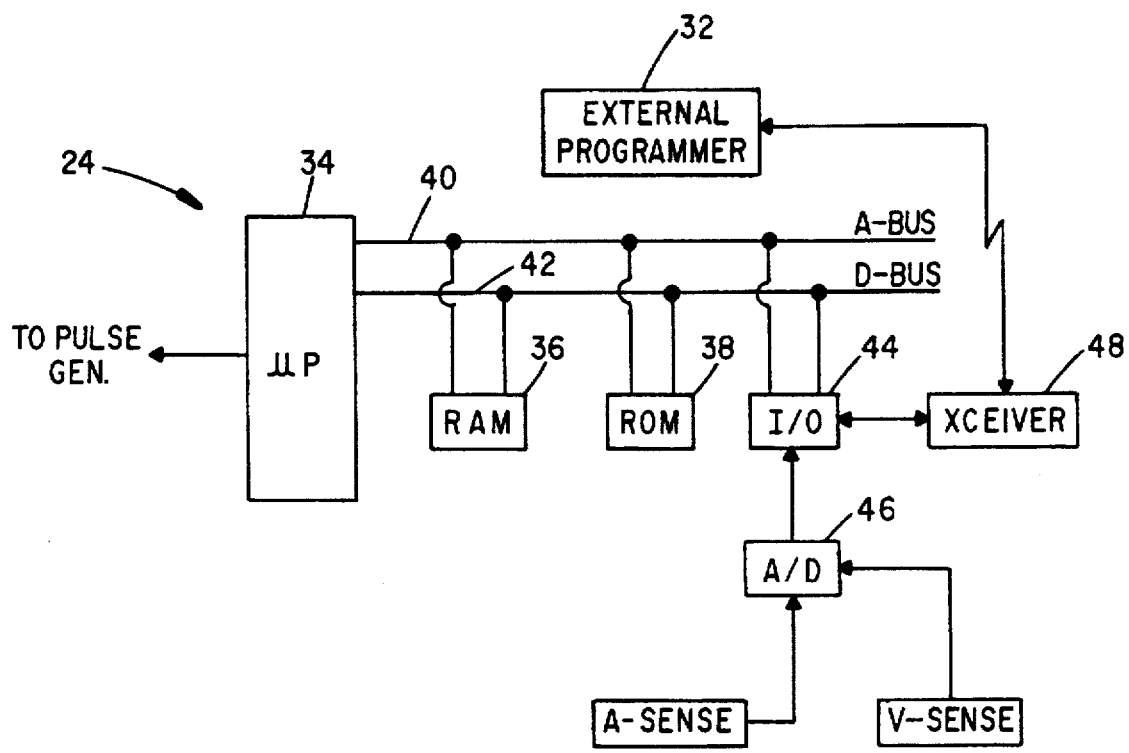
FIG. 2 is a schematic block diagram of the microprocessor-based controller incorporated into the pacemaker of FIG. 1.

FIG. 2 shows a more detailed block diagram of the microprocessor-based controller 24 shown in FIG. 1. It is conventional in its architecture and includes a microprocessor chip 34 and associated RAM and ROM memory modules 36 and 38 connected to it by an address bus 40 and a data bus 42. As is known in the art, the RAM memory 36 is a read/write memory comprising a plurality of addressable storage locations where multi-byte data words and operands used in the execution of one or more programs may be stored for subsequent readout. The ROM memory 38 will typically be used to store the control programs executable by the microprocessor chip 34.

Also connected to the address bus and data bus is an I/O interface module 44. If a separate analog-to-digital converter, as at 46, is utilized rather than an on-board A/D converter forming a part of the microprocessor chip 34, its output will be connected through the I/O module 44 allowing the analog outputs from the atrial sense amplifier 18 and the ventricular sense amplifier 22 to be digitized before being routed to the microprocessor chip 34. If the particular microprocessor employed incorporates an on-board A/D converter (as is somewhat conventional), then the outputs from the A-sense amplifier 18 and V-sense amplifier 22 would be applied directly to appropriate inputs of the microprocessor chip 34.

Also coupled to the I/O module 44 is a transceiver 48 that is used to interface the external programmer 32 to the implanted pacer 12. The manner in which an external programmer appropriately placed on the chest wall in proximity to the implanted device is capable of transmitting digitally encoded data therebetween is well known to those skilled in the art.

Figure 3:
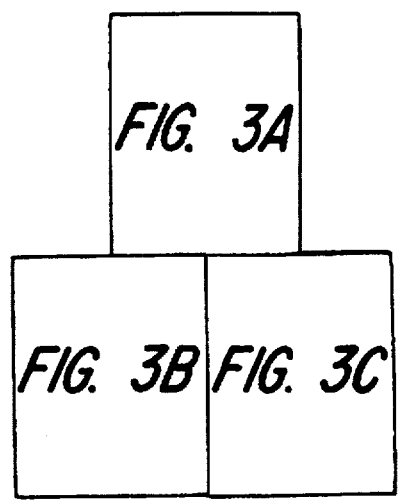
FIGS. 3A, 3B and 3C, when arranged as shown in FIG. 3, illustrate a flow diagram for the optimization algorithm of the present invention.
Figure 3A:
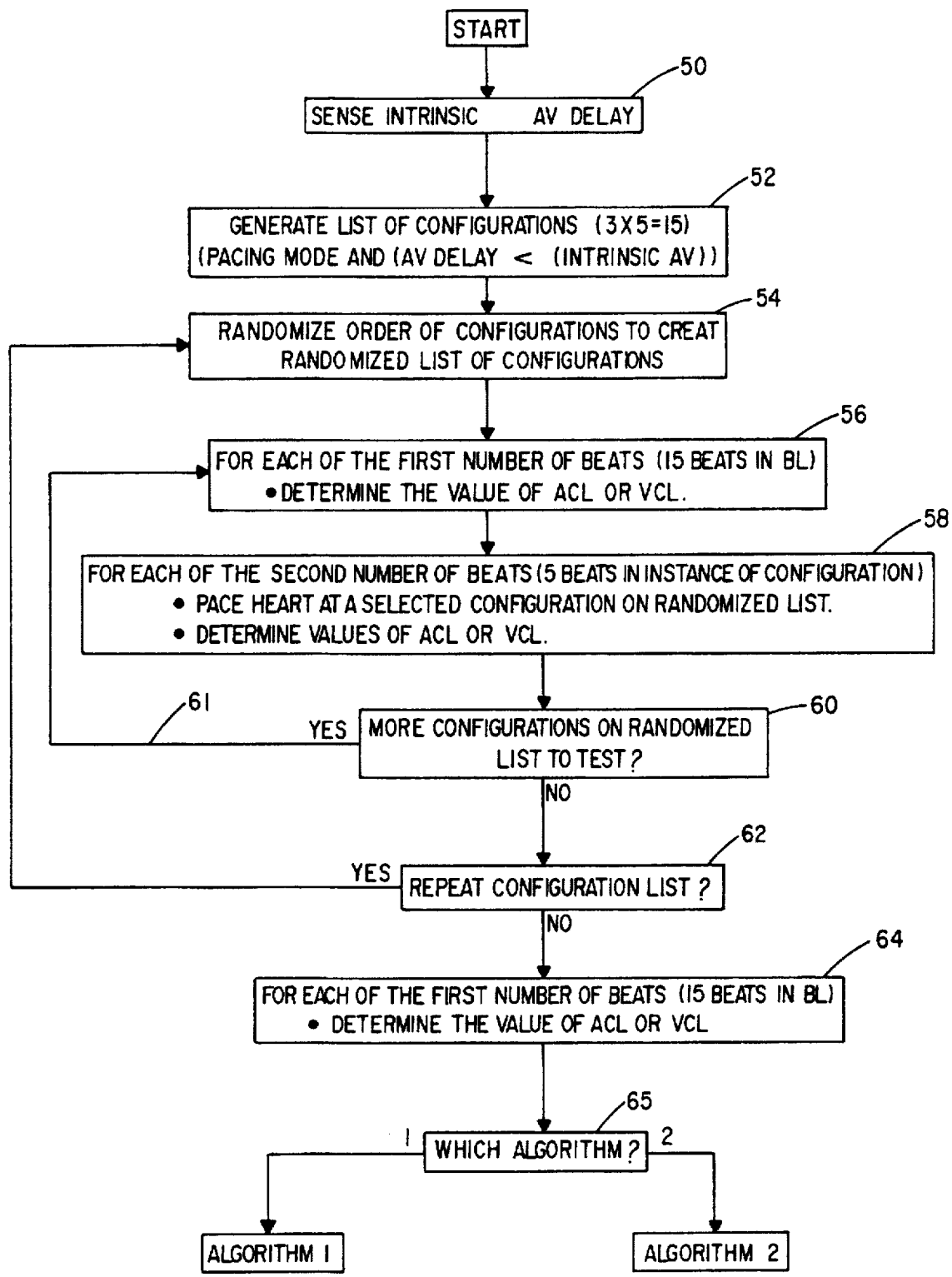
Figure 3B:
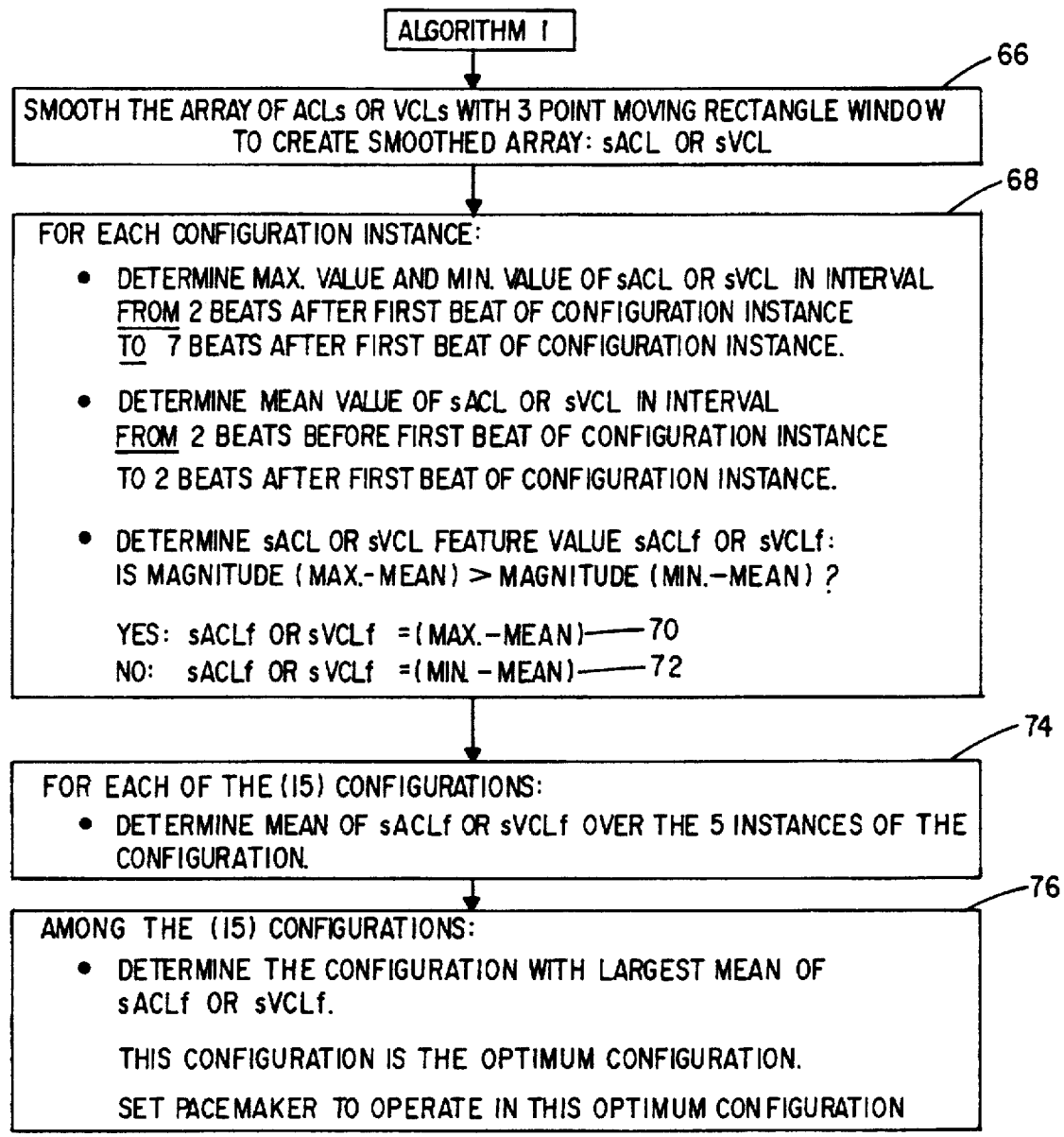
Figure 3C:
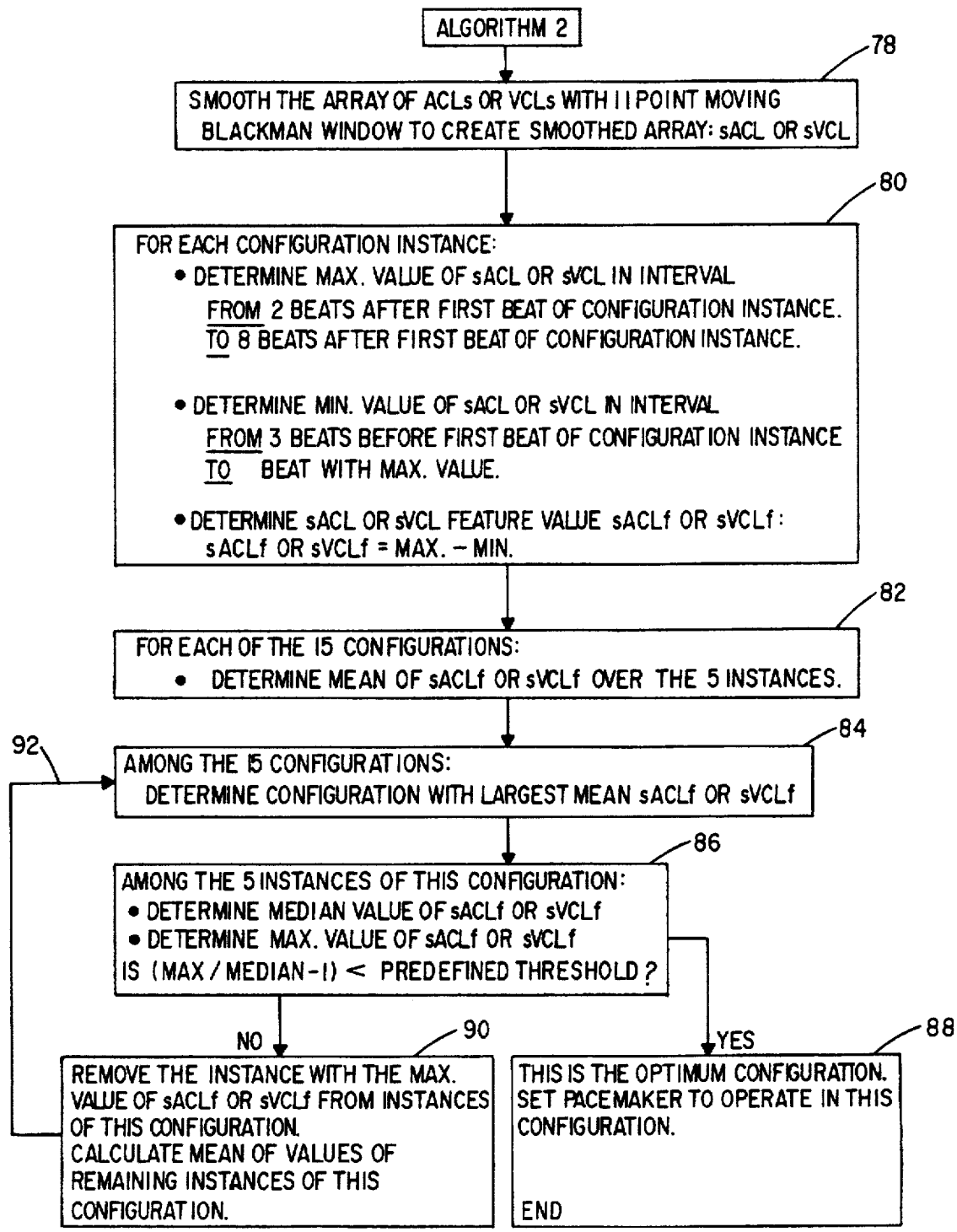

FIGS. 3A, 3B and 3C when arranged as shown in FIG. 3 comprise a flow chart of the algorithm executed by the microprocessor 34 in arriving at an optimal pacing mode-AV delay combination for a patient in which the system of the present invention is implanted.

Before explaining the steps of the algorithm in detail, a brief overview of the methodology is deemed helpful.

The algorithm can be executed by the microprocessor-based controller in the pacer or in an external microprocessor in the monitor/programmer 32. In the following description, it is assumed that the control algorithm is executed by the microprocessor 34 in the implanted device. The algorithm, using cardiac atrial cycle lengths measured in the VDD pacemaker, determines a patient's optimum pacing mode-AV delay, which is the mode (e.g., RV, LV, or BV) and AV delay during VDD pacing which maximizes cardiac function (e.g., pulse pressure) for the patient. The pulse generator 26 is then set to operate at this optimum pacing mode-AV delay.

The optimal pacing mode-AV delay is determined from the maximum (or minimum) value of one of several empirically derived features which are calculated from the atrial cycle lengths. In particular, the atrial cycle lengths immediately following a transition from an intrinsic or paced baseline (BL) to a paced mode-AV delay, i.e., during a transient period of the paced mode-AV delay, is used. Thus, this invention eliminates the need for a period of waiting for hemodynamic stability to be reached during the paced mode-AV delay.

The pulse generator will be made to cycle through a predetermined number of intrinsic or paced BL beats followed immediately by paced beats using a first mode-AV delay configuration, followed immediately by additional intrinsic or paced BL beats, followed immediately by beats of a second mode-AV delay configuration, etc., until all of the possible configurations have been utilized. The ACL between successful beats is computed and stored as an array in the RAM memory of the microprocessor-based controller.

Once the array of ACL values are stored, they are subsequently processed to arrive at values of ACL features. In particular, the array of values may be smoothed using a 3-point moving rectangle window or an 11-point moving Blackman window. Then for each configuration and repeated instances thereof, further computations are made to identify the particular configuration exhibiting the largest average of the smoothed ACL features. It is this configuration that is determined to be the optimum and the pacemaker is then set to operate in this optimum configuration. The automatic selection of optimal mode-AV delay which is found to optimize cardiac function eliminates any need for manual programming of the implanted pacemaker by the physician.

The algorithm of the present invention is based upon a hypothesis that if a transient change in atrial cycle length is large positive, then the transient change in aortic pulse pressure is also large positive. Thus, the largest positive change in atrial cycle length predicts the largest positive change in aortic pulse pressure.

There is a physiological basis for this relationship. A large, sudden increase in the aortic pressure (in this case due to the sudden change from baseline cardiac function to paced mode-AV delay cardiac function) is sensed by arterial baroreceptors, and the reflex mechanism of the Autonomic Nervous System (ANS) tries to drive the aortic pressure back to its previous stable (in this case, baseline) value by increasing the atrial cycle length. The ANS acts as a negative feedback control system for the aortic pressure.

The paced mode-AV delay associated with the largest increase in ACL is hypothesized to be the optimum paced mode-AV delay for the pacemaker. The optimum is the one that provides a maximum increase in aortic pressure over baseline aortic pressure.

With the foregoing summary in mind, then, attention is directed to the flow charts of FIGS. 3A, 3B and 3C. As reflected in block 50 in FIG. 3A, the pulse generator is initially inhibited while intrinsic cardiac activity is sensed such that a value of the patient's intrinsic AV delay can be measured. Next, the physician may generate a list of all possible combinations of three pacing modes and a predetermined number of AV delay values where each of the delay values is set to be less than the intrinsic AV value measured at block 50. While a different number of paced AV delay values can be selected, for purposes of explanation of the inventive algorithm, it will be assumed that five different AV values less than the intrinsic value are established by the physician. This leads to 3×5=15 possible configurations as indicated in block 52.

To avoid any influence that the particular order in which the configurations are employed in pacing the patient, the list generated in step 52 is randomized as reflected in block 54 in FIG. 3A.

Again, without limitation, a string of beats with the pulse generator inhibited may be used to establish BL and then for each of these baseline beats, the atrial cycle length between them is determined. As earlier mentioned, rather than using intrinsic cardiac rhythm to establish BL, the BL can also be at a particular paced rate and pacer mode. In the description to follow, a group of 15 sequential beats are generated. The ACL measurement may be performed in the microprocessor by initiating a timer upon the occurrence of a P-wave in the cardiac electrogram and stopping the timer upon detection of the next succeeding P-wave. The ACL value associated with each beat is then stored as an array in the RAM memory 36. Immediately following the last of the 15 beats used in establishing BL, the heart is paced using a selected configuration drawn from the randomized list developed at block 54. Again, without limitation, the second number of beats may equal five. As with the BL beats, the ACL for the paced beats is also determined as reflected in block 58.

A test is next made at block 60 to determine whether all of the 15 possible configurations on the randomized list have been used and the ACL values associated therewith stored in the memory. See block 60.

If not all of the configuration possibilities have been exhausted, control returns over path 61 to block 56 and the operations reflected in blocks 56 and 58 are repeated until all of the possibilities have been exhausted. So that any anomalies which may have occurred in the measurement of the respective ACL values can be averaged out, steps 54, 56, 58 and 60 are repeated a predetermined number of times, e.g., five times, to obtain additional instances of the configurations that can later be averaged. See decision block 62.

The change in pulse pressure caused by the five paced beats in step 58 is immediate: There is no time delay. However, the change in ACL caused by the reflex mechanism of the Autonomic Nervous System in response to this change in pulse pressure is not immediate: There is a time delay of several beats. Thus, the delayed change in ACL can occur during the 15 BL beats in step 56 which follow the five paced beats in step 58. Thus, the final 15 BL beats in step 64 are needed to follow the final five paced beats in step 58.

Once the raw ACL values have been computed and stored as an array in the RAM memory, one or the other of two possible algorithms may be used to further process the raw data in arriving at the particular pacing mode-AV delay configuration yielding optimum hemodynamic performance. Algorithm 1 and Algorithm 2 are illustrated in FIGS. 3B and 3C. Algorithm 2 is better because it gives better results over the patients tested. However, the two patients with the smallest (<3.8 ms) max mean ACL feature values had poor results with Algorithm 2. The two patients had good results with Algorithm 1 Strategy: (1) Use Algorithm 2. (2) If the max mean ACL feature value is small (less than a predefined threshold, e.g. 3.8 ms), ignore Algorithm 2 results and run Algorithm 1. In addition to the strategy, it may prove expedient to have Algorithm 1 and the Algorithm 2 physician selectable.

The first step in Algorithm 1 in FIG. 3B is to smooth the array of ACLs with a 3-point moving rectangle window with the thus smoothed values also being stored in the RAM memory as a smoothed array referred to as "sACL". While other smoothing techniques are known to persons skilled in signal processing, the 3-point moving rectangle window technique is fairly simple to execute and has been found to produce reliable results. This smoothing step is identified by block 66 in FIG. 3B.

Figure 4:
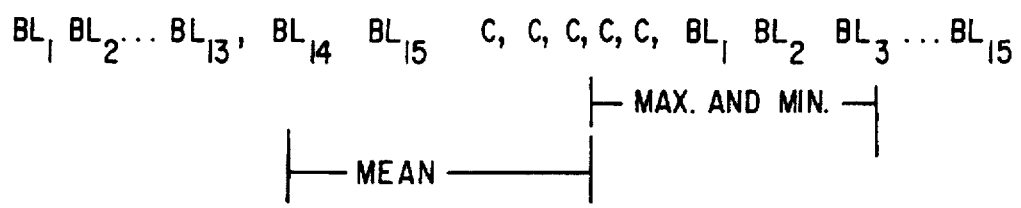
FIG. 4 is a representation of a series of baseline and paced beats useful in explaining the development of ACL features in accordance with a first algorithm.

Referring next to block 68, for each of the 15×5=75 mode-AV configuration instances, the maximum value and the minimum value of the smoothed ACL in an interval from two beats after the first beat of the configuration instance to seven beats after the first beat of the configuration instance are computed. This operation is further explained with the aid of FIG. 4. In FIG. 4 there is shown a series of 15 baseline beats followed by five paced beats of an instance of a first configuration identified as $C_1$, again followed by another series of 15 baseline beats. The interval in which the maximum and minimum values of smoothed ACLs are to be located is labeled "MAX and MIN". Likewise, the interval in which the mean value of smoothed ACLs is to be located is identified by "MEAN". By selecting the intervals in the manner indicated, changes in ACL of a transient nature as distinguished from steady state is guaranteed.

Once the MAX and MIN values of sACL for the configuration instance have been arrived at, a test is made to determine whether the absolute value of the quantity (MAX−MEAN) is greater than the absolute value of the quantity (MIN−MEAN) for the configuration instance. If the outcome of the test is true, then the smoothed ACL feature (sACLf) for the configuration instance is determined to be the quantity (MAX−MEAN). If the test is false, then sACLf is made to be (MIN−MEAN). See steps 70 and 72.

Next, as indicated by operation block 74, for each of the 3×5=15 possible configurations, a computation is made to determine the average or mean of the sACLf over the five repeated instances of the configuration. Once the operation indicated by block 74 has been completed, the particular configuration exhibiting the greatest mean of smoothed ACL features is identified, and the pacemaker is automatically programmed to operate with this optimum configuration. See block 76.

Figure 5:
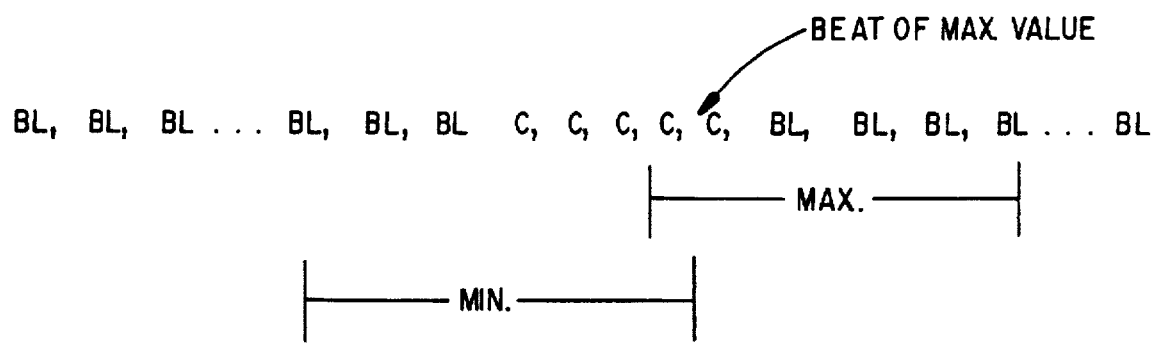
FIG. 5 is a drawing similar to FIG. 4 for a second algorithm.

An alternative algorithm processing the raw ACL data resulting from the execution of the data gathering steps reflected by blocks 50–64 in the flow chart of FIG. 3A is illustrated in FIG. 3C. Again, the raw ACL data are first smoothed using a different known signal processing approach referred to as an 11-point moving Blackman window yielding a smoothed ACL array: sACL (block 78). For each of the five instances of each of the 15 configurations of pacing mode and AV delay (yielding a total of 15×5=75 configuration instances), the maximum value of sACL values in an interval from two beats after the first beat of a configuration instance to eight beats after the first beat of the configuration instance is determined. Likewise, a minimum value of sACL values in an interval from three beats before the first beat of the configuration instance to the beat with the maximum value is determined. FIG. 5 is helpful in defining the respective intervals in which the maximum values and minimum values are to be found. Once the maximum value and minimum value in the respective intervals have been determined, a smoothed ACL feature value (sACLf) is computed as the maximum value minus the minimum value. The respective operations referred to above are identified in block 80 of the flow diagram of FIG. 3C.

Upon completion of step 80, for each of the 15 possible configurations of mode and AV delay, the mean of the sACLf values of the five repeated instances of the configuration is computed. See block 82. Next, out of the 15 possible configurations, the configuration exhibiting the largest mean sACLf is computed (block 84).

Once the particular configuration exhibiting the largest mean sACLf is arrived at via step 84, the five instances where this particular configuration has been repeated are examined to determine a median value and a maximum value of the smoothed ACL feature sACLf. With the median and maximum values so determined, a test is made to determine whether the quantity (MAX/MEDIAN−1) is less than a predefined threshold.

The intent of this threshold test is to remove a MAX whose value is too large (relative to the MEDIAN value). The "predefined threshold" has a value of 9.5, which gives good results for the set of patients investigated. The value 9.5 was determined heuristically from the patients tested. If the result of the test is true, the optimum configuration has been arrived at and the pacemaker is set to operate in this configuration (block 88). If the test of block 86 had proved false, the five instances for the configuration having the largest mean will have the instance with the maximum value removed, and the mean of the values of the remaining four instances for this configuration is calculated. See block 90. Control then passes over line 92 to again repeat steps 84 and 86 until such time as the test set out in block 86 comes out true.

Patient tests have shown that the relatively easy-to-measure atrial cycle length (or ventricular cycle length) can be used to automatically determine the pacing mode-AV delay configuration which provides pulse pressures greater than the pulse pressure achieved with baseline cardiac performance. Thus, the need for a special sensor to actually measure pulse pressure itself, which is difficult to measure, is eliminated.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. As already mentioned, the intrinsic and paced beat information can readily be telemetered out to an external programmer/monitor incorporating a microprocessor and associated memory so that the ACL determinations and signal processing thereof can be done external to the patient in arriving at the optimal pacing mode-AV delay interval. Hence, the scope of the invention is to be determined from the appended claims.

What is claimed is:

1. A method of optimizing the AV delay and pacing mode configuration of a dual chamber pacemaker of the type having means for sensing atrial depolarization events, means for sensing ventricular depolarization events and means for applying cardiac stimulating pulses selectively to the right, left or both ventricular chambers at predetermined AV delay intervals following detection of atrial depolarization events, comprising the steps of:

(a) tracking a patient's intrinsic atrial depolarization events;

(b) measuring the patient's atrial cycle length (ACL) between successive atrial depolarization events over a first predetermined number of heart beats, $N_1$, at a first AV delay interval and storing the measured ACLs as an array in a memory to establish a baseline value;

(c) changing at least one of AV delay interval and pacing mode configuration by changing, for a second predetermined number of heart beats, $N_2$, less than the first predetermined number of heart beats, (i) the AV delay interval of the pacemaker from the baseline value to a different AV delay interval less than the value at which intrinsic is established, or (ii) the ventricle(s) to which the stimulating pulses are applied;

(d) measuring the patient's ACLs between successive atrial depolarization events over the second predetermined number of heart beats and storing the measuring ACLs in the array in said memory;

(e) calculating and storing an ACL feature value obtained from the patient's atrial cycle length measured in steps (b) and (d);

(f) repeating steps (a)–(e) in iterative cycles over a range of AV delay intervals and ventricular chamber(s) selected for receiving the cardiac stimulating pulses;

(g) after step (f) for each pacing mode-AV delay configuration calculating the average of the ACL features over all of the occurrences of the configuration;

(h) determining the optimal configuration from among the averages determined in step (g); and (i) setting the AV delay and pacing mode configuration of the pacemaker to the optimal AV delay and pacing mode configuration established in step (h).

2. The method of claim 1 wherein the ACL feature value is calculated by the steps of:

(j) smoothing the array of ACLs;

(k) determining from the smoothed array of ACLs a maximum value and a minimum value in a first predetermined interval measured in beats for each AV and pacing mode configuration;

(l) determining from the smoothed array a mean value of ACLs in a second predetermined interval measured in beats for each AV delay and pacing mode configuration;

(m) computing an absolute value of the difference between said maximum value and said mean value and computing an absolute value of the difference between said minimum value and said mean value;

(n) comparing the absolute value of the difference between the maximum value and the mean value with the absolute value of the difference between the minimum value and the mean value to determine which is the larger; and (o) setting the ACL feature value to the difference between the maximum value and the mean value when the absolute value of that difference is greater than the absolute value of the difference between the minimum value and the mean value, and setting the ACL feature value to the difference between the minimum value and the mean value when the absolute value of the difference between the maximum value and the mean value is less than or equal to the absolute value of the difference between the minimum value and the mean value.

3. A method for optimizing the AV delay interval and pacing mode configuration of a programmable dual chamber cardiac pacemaker of the type having means for sensing atrial and ventricular depolarization events, including a microprocessor-based controller for selectively stimulating the right, the left or both ventricular chambers with pacing pulses at predetermined AV delay intervals following detection of atrial depolarization events, the microprocessor-based controller having means for determining atrial cycle lengths and a memory for storing data in an addressable array, comprising the steps of:

(a) storing in the memory a listing of pacing mode and AV delay configurations, each such configuration specifying ventricular chamber(s) to be stimulated and an AV delay interval to be utilized;

(b) pacing the ventricular chamber(s) in accordance with a pacing mode AV delay configuration selected randomly from said listing for a first number of beats, $N_1$, following a second number of intrinsic beats, $N_2$, sufficient to establish a base line;

(c) repeating step (b) for each pacing mode and AV delay configuration contained in the listing;

(d) determining the ACL values between each of the $N_1$ and $N_2$ beats resulting from steps (b) and (c) and storing said ACL value in the addressable array in the memory;

(e) repeating steps (b) through (d) a predetermined number of instances, $N_3$;

(f) smoothing the array of ACLs;

(g) determining for all $N_3$ instances of each pacing mode and AV delay configuration the maximum value of the smoothed ACLs in a first interval beginning after a change to the first number of beats $N_1$ and ending after a change to the second number of beats, $N_2$, and a minimum value of the smoothed ACLs in a second interval beginning a predetermined number of beats prior to a change from the $N_2$ beats to the $N_1$ beats and ending with the beat associated with the maximum value;

(h) computing a smoothed ACL feature as the difference between the maximum value and the minimum value;

(i) calculating the mean value of the smoothed ACL features computed in step (h) over the $N_3$ instances for each pacing mode AV delay configuration and determining the configuration yielding the largest mean value;

(j) determining among the $N_3$ instances associated with the configuration yielding the largest mean value a median value and a maximum value of smoothed ACL features; and (k) programming the pacemaker to the configuration determined in step (i) when the difference between the ratio of maximum value and the median value is less than a predetermined value.

4. The method of claim 3 and when the ratio of maximum value and the median value of smoothed ACL features is greater than or equal to the predetermined threshold value, repeating steps (i) and (j) after recalculating the mean of the instances of the configuration associated with the largest mean value of smoothed ACL features after removing the instance having the maximum value of smoothed ACL features from the instances.

5. A method of optimizing the AV delay and pacing mode configuration of a dual chamber pacemaker of the type having means for sensing atrial depolarization events, means for sensing ventricular depolarization events and means for applying cardiac stimulating pulses selectively to the right, left or both ventricular chambers at predetermined AV delay intervals following detection of atrial depolarization events, comprising the steps of:

(a) tracking a patient's intrinsic ventricular depolarization events;

(b) measuring the patient's ventricular cycle length (VCL) between successive ventricular depolarization events over a first predetermined number of heart beats, $N_1$, at a first AV delay interval and storing the measured VCLs as an array in a memory to establish a baseline value;

(c) changing at least one of AV delay interval and pacing mode configuration by changing, for a second predetermined number of heart beats, $N_2$, less than the first predetermined number of heart beats,
 (i) the AV delay interval of the pacemaker from the baseline value to a different AV delay interval less than the value at which intrinsic is established;
 (ii) the ventricle(s) to which the stimulating pulses are applied;

(d) measuring the patient's VCLs between successive ventricular depolarization events over the second predetermined number of heart beats and storing the measured VCLs in the array in said memory;

(e) calculating and storing a VCL feature value obtained from the patient's ventricular cycle length measured in steps (b) and (d);

(f) repeating steps (a)–(e) in iterative cycles over a range of AV delay intervals and ventricular chamber(s) selected for receiving the cardiac stimulating pulses;

(g) after step (f) for each pacing mode-AV delay configuration calculating the average of the VCL features over all of the occurrences of the configuration;

(h) determining the optimal configuration from among the averages determined in step (g); and (i) setting the AV delay and pacing mode configuration of the pacemaker to the optimal AV delay and pacing mode configuration established in step (h).

6. The method of claim 5 wherein the VCL feature value is calculated by the steps of:

(j) smoothing the array of VCLs;

(k) determining from the smoothed array of VCLs a maximum value and a minimum value in a first predetermined interval measured in beats for each AV and pacing mode configuration;

(l) determining from the smoothed array a mean value of VCLs in a second predetermined interval measured in beats for each AV delay and pacing mode configuration;

(m) computing an absolute value of the difference between said maximum value and said mean value and computing an absolute value of the difference between said minimum value and said mean value;

(n) comparing the absolute value of the difference between the maximum value and the mean value with the absolute value of the difference between the minimum value and the mean value to determine which is the larger; and (o) setting the VCL feature value to the difference between the maximum value and the mean value when the absolute value of that difference is greater than the absolute value of the difference between the minimum value and the mean value, and setting the VCL feature value to the difference between the minimum value and the mean value when the absolute value of the difference between the maximum value and the mean value is less than or equal to the absolute value of the difference between the minimum value and the mean value.

7. A method for optimizing the AV delay interval and pacing mode configuration of a programmable, dual-chamber, cardiac pacemaker of the type having means for sensing atrial and ventricular depolarization events, including a microprocessor-based controller for selectively stimulating the right, the left or both ventricular chambers with pacing pulses at predetermined AV delay intervals following detection of atrial depolarization events, the microprocessor-based controller having means for determining ventricular cycle lengths (VCLs) and a memory for storing data in an addressable array, comprising the steps of:

(a) storing in the memory a listing of pacing mode and AV delay configurations, each such configuration specifying ventricular chamber(s) to be stimulated and an AV delay interval to be utilized;

(b) pacing the ventricular chamber(s) in accordance with a pacing mode-AV delay configuration selected randomly from said listing for a first number of beats, $N_1$, following a second number of intrinsic beats, $N_2$, sufficient to establish a baseline;

(c) repeating step (b) for each pacing mode and AV delay configuration contained in the listing;

(d) determining the VCL values between each of the $N_1$ and $N_2$ beats resulting from steps (b) and (c) and storing said VCL value in the addressable array in the memory;

(e) repeating steps (b) through (d) a predetermined number of instances, $N_3$;

(f) smoothing the array of VCLs;

(g) determining for all $N_3$ instances of each pacing mode and AV delay configuration the maximum value of the smoothed VCLs in a first interval beginning after a change to the first number of beats, $N_1$, and ending after a change to the second number of beats, $N_2$, and a minimum value of the smoothed VCLs in a second interval beginning a predetermined number of beats prior to a change from the $N_2$ beats to the $N_1$ beats and ending with the beat associated with the maximum value;

(h) computing a smoothed VCL feature as the difference between the maximum value and the minimum value;

(i) calculating the mean value of the smoothed VCL features computed in step (h) over the $N_3$ instances for each pacing mode-AV delay configuration and determining the configuration yielding the largest mean value;

(j) determining among the $N_3$ instances associated with the configuration yielding the largest mean value a median value and a maximum value of smoothed VCL feature; and (k) programming the pacemaker to the configuration determined in step (i) when the difference between the ratio of maximum value and the minimum value is less than a predetermined value.

8. The method of claim 7 and when the ratio of maximum value and the median value of smoothed VCL features is greater than or equal to the predetermined threshold value, repeating steps (i) and (j) after recalculating the mean of the instances of the configuration associated with the largest mean value of smoothed VCL features after removing the instance having the maximum value of smoothed VCL features from the instances.

* * * * *